United States Patent [19]

Pate et al.

[11] 4,166,385
[45] Sep. 4, 1979

[54] NON-ADIABATIC REACTION CALORIMETRIC TECHNIQUE

[75] Inventors: Kevin T. Pate, Midland; Edward E. Timm, Coleman, both of Mich.

[73] Assignee: The Dow Chemical Company, Midland, Mich.

[21] Appl. No.: 919,885

[22] Filed: Jun. 28, 1978

[51] Int. Cl.² ............................................. G01K 17/00
[52] U.S. Cl. .............................. 73/190 R; 23/230 PC; 422/51
[58] Field of Search ................. 73/190 R; 23/230 PC; 422/51

[56] References Cited

U.S. PATENT DOCUMENTS

| | | | |
|---|---|---|---|
| 3,667,294 | 6/1972 | Schoenlaub | 73/190 |
| 4,054,056 | 10/1977 | Wegstedt | 73/190 |
| 4,088,447 | 5/1978 | Walker | 73/190 X |

Primary Examiner—Herbert Goldstein
Attorney, Agent, or Firm—Burke M. Halldorson

[57] ABSTRACT

A nonadiabatic calorimetric technique useful broadly for quantifying the reaction kinetics of thermally unstable solids is based on the distinguishing mode of establishing, under near steady state conditions, a thermal gradient across a reaction sample contained between monitored hot and cold surfaces, stepwise or rampwise increasing the temperature of the hot surface, and quantifying the maximum temperature that is withstood by the sample at the inception condition of a thermal runaway reaction. The critical hot surface temperature recorded by the experiment is a function of the cold surface condition, i.e., the applied thermal gradient. At least two critical hot surface temperatures, which are required for calculations, are generated by repeating the experiment under differing cold surface conditions. Solution of the steady-state differential equation describing the system, utilizing the experimental data, yields the general kinetics of the decomposition reaction of the tested solid. These thusly known kinetics allow prediction of the unsteady-state adiabatic or nonadiabatic thermal decomposition of the solid for any product geometry and initial condition.

1 Claim, 1 Drawing Figure

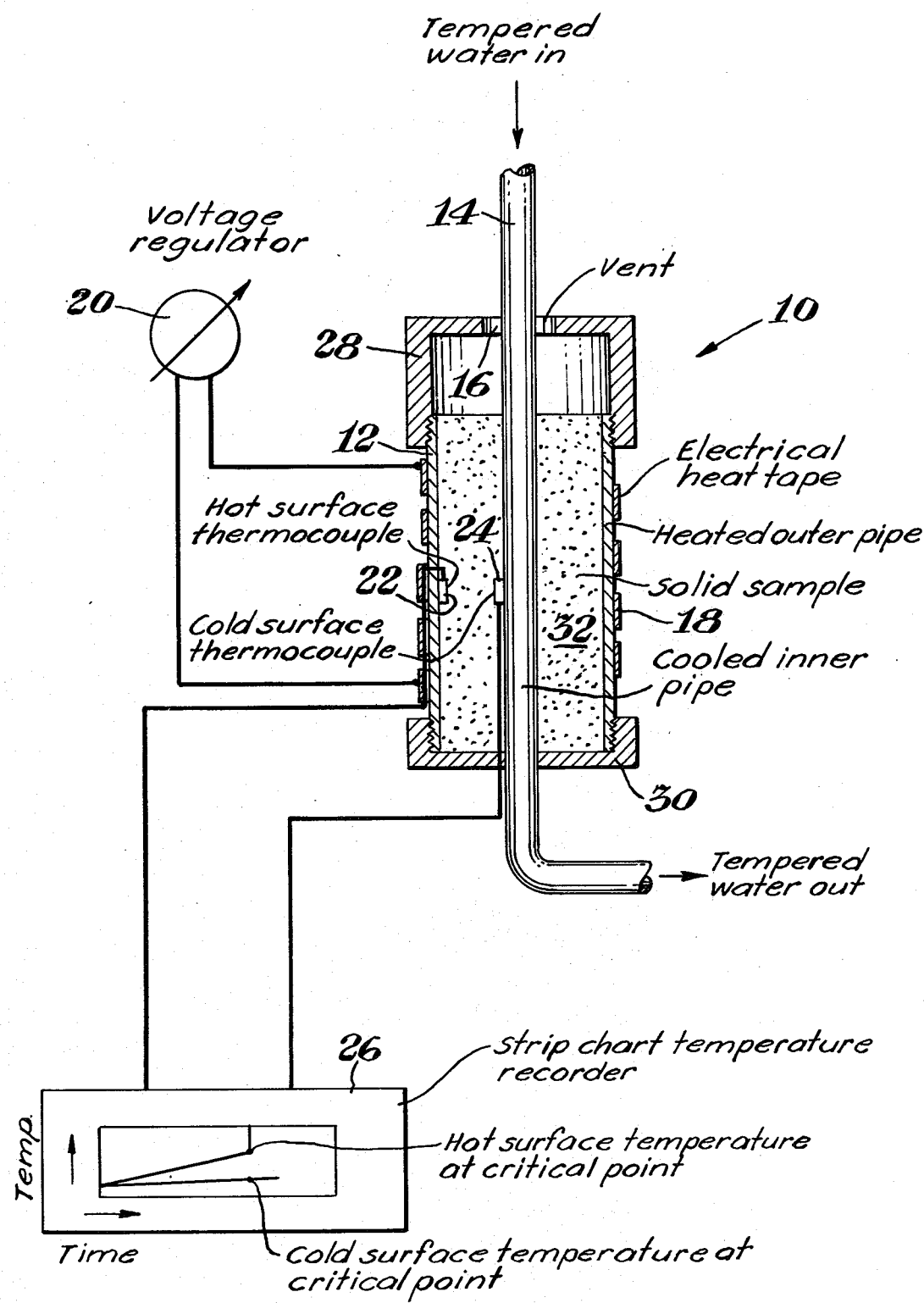

NON-ADIABATIC REACTION CALORIMETRIC TECHNIQUE

FIELD OF THE INVENTION

The invention is in the field of calorimetric analysis. More particularly, the invention relates to an improved technique for yielding the kinetics of the decomposition reaction of thermally unstable solids. The information developed by the invention is used to predict inherent thermal hazards occurring with materials handling and production, and to develop precautionary techniques in respect thereto.

BACKGROUND OF THE INVENTION

Thermal decomposition is a serious potential accident hazard in the production and storage of thermally unstable chemicals. The characteristic reaction of a decomposing chemical evolves large quantities of heat. Under near adiabatic or well insulated conditions, the material is thus capable of sustaining a thermal runaway. The phenomenon is defined by the exponential nature of the reaction kinetics with respect to temperature. Solids, which tend to become self-insulated from their surroundings because of their low heat transfer characteristics, are particularly susceptible to incurring a thermal runaway.

Precautionary methods include the use of calorimetric anaylsis to evaluate the relative stability of reactive chemicals. The goal of the analysis is to develop an accurate knowledge of the kinetics of the decomposition reaction and heat transfer characteristics of the material. Once these parameters are known, prediction of the adiabatic or nonadiabatic thermal runaway curve is possible. This information is then used to determine safe operating and storage conditions for the material.

Generally, excellent calorimetric techniques are available for developing quantitative hazard information for predicting the behavior of thermally unstable liquids and vapors. The accelerating rate calorimeter (ARC) from Columbia Scientific Industries, Austin, Texas, is considered exemplary of the most advanced state of the prior art.

Basically the ARC consists of a contained sample which is allowed to undergo an adiabatic thermal runaway within a confines of the bomb container. Time-temperature data from this runaway is used to calculate the general kinetics describing the decomposition reaction. This information is then used for hazard prediction.

An assumption of the ARC is that the sample is a well-mixed system with good thermal contact between the sample and bomb container. Solids which characteristically have low thermal conductivity, and thus a marked tendency to heat non-uniformly, therefore, become a problem in the ARC even at low self-heat rates. Since the measuring thermocouple is located on the external surface of the bomb, the ensuing time-temperature data of the bomb thus may not accurately reflect what the sample actually underwent. Also, since the solid sample is not well mixed and has low heat transfer characteristics, the temperature throughout the solid sample itself may not be satisfactorily uniform. Imbedding the thermocouple directly in the sample, therefore, can still yield inaccurate and nonreproducible results. The same problems that occur with solid samples in the ARC also tend to occur in other prior state of the art calorimeters since similar assumptions are made. Such devices are thus generally poorly suited to adequately account for the low thermal conductivity characteristics of solid samples, hence tending to introduce errors in the data generated by the experiment.

THE INVENTION

The calorimetric technique of the invention operates under a completely different principle than the ARC and other calorimeters. It is designed specifically for thermally unstable solid materials, generally, and takes into account their low heat transfer characteristics. Basically, the inventive technique utilizes a heat transfer device wherein a reactive sample is confined between hot and cold surfaces. The principle consists of applying a controlled, known thermal gradient across the sample. The temperature of the hot surface is stepwise or rampwise increased, observing the required condition of maintaining a near steady state condition. Thus, with each incremental temperature advance, the system is allowed to equilibrate to establish a steady state thermal gradient or temperature distribution across the sample. The steady state condition is critically observed as the decomposing sample approaches the maximum temperature it can withstand without undergoing a thermal runaway. The temperature at the hot surface where the system becomes unstable is the critical temperature for that applied gradient.

Critical temperature points generated by the experiment are used with differential equation analysis to quantify the decomposition reaction kinetics of the decomposing sample. The information may then be used, as an example, to predict the unsteady state adiabatic runaway curve i.e., the worst hazard condition of the tested material. Other useful information concerning the unsteady state non-adiabatic runaway potential, for any product geometry and initial condition, may also be generated and used as a quideline for the safe production and storage of the material.

The invention is susceptible to use with various designs of calorimeters, which basically employ the common elements of temperature controlled hot and cold surfaces with heat sensing elements. Accurate temperature detection is required closely adjacent to the hot surface, and a second detection point is most conveniently located adjacent to the cold surface, but may be located elsewhere at a known position.

The geometry of the calorimeter may assume a rectangular design, that is, one hot plate and one cold plate with the sample contained in the space between the two plates. More practical in operation, however, is a cylindrical design with the sample contained between two concentric pipes. The cylindrical design is more efficient than the rectangular design since the outer pipe acts as a sample container and also minimizes external heat loss from the sample to the surroundings. A spherical design, that is, one spherical surface inside another spherical surface with the sample between the spheres, is impractical both in design and operation, but except for the physical inconveniences, such a system may also be suitably employed.

Two basic versions of the preferred cylindrical design are possible. One design consists of the outer pipe being the cold surface and the inner pipe being the hot surface. The other design consists of the outer pipe being the hot surface and the inner pipe being the cold surface. The latter is the superior design. It is more sensitive for detecting exothermic reactions since it entails a relatively large amount of hot sample reacting and conducting its heat to a small thermal sink.

The calorimeter used in the experiment either can be sealed and frangibled or can be vented for operation at ambient pressure conditions. An inert atmosphere for the sample is possible by purging the calorimeter with an inert gas after sample loading is complete. The calorimeter must be sealed in this case to prevent air from re-entering the sample during the experiment. Use of a sealed and thus frangibled sample reaction chamber would be desirably employed, for example, to determine the effect of pressure on the decomposition kinetics of a given sample. Similarly an inert or controlled gas environment may be used in the experiment to determine what effect, for example, nitrogen blanketing might have on the decomposition kinetics, which information may be used in developing safer techniques for the drying or other handling of unstable solid compositions.

BRIEF DESCRIPTION OF THE DRAWING

The drawing is an elevational view with parts in cross section of a preferred design of a calorimeter adapted for operation in the mode of the invention.

DETAILED DESCRIPTION OF THE PREFERRED EMBODIMENT

The calorimeter 10 illustrated is of the preferred cylindrical design with an outer pipe 12 as the hot surface, and a concentric inner pipe 14 as the cold surface. This is the vented design which operates under ambient pressure by venting the decomposition gases through an annular opening or vent 16. The outer pipe is heated by an electrical heat tape 18 which is wrapped evenly around its outside surface. Heat input is controlled by a voltage regulator 20. The inner pipe is cooled by tempered water. Tempered water is employed so that different thermal gradients can be attained in the calorimeter by varying the temperature of the inner pipe. The temperature of the inside hot surface and outside cold surface, the surfaces that the sample is exposed to, are monitored by small diameter, sheathed thermocouples 22, 24 connected to a strip chart temperature recorder 26. Cap elements 28, 30 are threadably affixed to each end of the outer pipe and include axially positioned openings through which the inner pipe is inserted in making the assembly. The lower cap element is welded to the inner pipe to form a hermitic seal. The combination defines a cylindrical sample reaction chamber 32. The preferred material of construction is stainless steel for all elements.

OPERATION

A filling amount of product is loaded into the calorimeter and the top of the calorimeter is installed. Cooling water is introduced into the inner pipe. A low power input is applied to the outer heater 18. This gradually heats up the outer pipe until the heat transfer through the sample equals the power input from the heater, thus reaching equilibrium. From this data and prior calibration with a material of known heat transfer characteristics, the thermal conductivity of the sample is determined using Fourier's Law (unless the value for that sample is available from the literature).

A slow ramp or stepwise increment is started on the outer heater by adjusting the voltage regulator. The ramp or step-up heating mode must be gradual so that the system will be very close to steady-state conditions.

The temperatures of the hot and cold surfaces are continually monitored throughout the ramp. As the temperature of the hot surface is increased, the reactive sample exothermically generates heat at an increasing rate. At some temperature, the rate of heat generation by reaction will exceed the ability of the solid to conduct the heat away to the cold surface. The system then becomes unstable and undergoes a thermal runaway. The temperature at the hot surface where the system becomes unstable is the critical temperature for that applied gradient. This hot surface temperature and corresponding cold surface temperature at the critical point establish one data point, or set of boundary conditions, for use in solving the differential equation describing the system. The calorimeter is then cooled, dismantled, and cleaned for the next experiment.

The calorimeter is again loaded with the same sample material. Conditions for the second experiment are changed to obtain a different thermal gradient across the sample. This is accomplished by flowing hotter or colder water through the inside pipe. A gradual ramp or step-up heating is started and the critical point is observed for this second condition.

Using these two critical data points, or boundary conditions, the appropriate differential equation below describing the calorimeter system is solved numerically by computer analysis to determine the kinetic parameters of the decomposition reaction.

Cylindrical coordinates (Applicable to the Preferred Embodiment):

$$\rho C_p \frac{\partial T}{\partial \theta} = \rho(-\Delta H_R)a e^{-\Delta E/RT} + k \frac{1}{r} \frac{\partial}{\partial r}\left(r \frac{\partial T}{\partial r}\right) \quad \text{Equation 1A}$$

Rectangular coordinates:

$$\rho C_p \frac{\partial T}{\partial \theta} = \rho(-\Delta H_R)a e^{-\Delta E/RT} + k \frac{\partial^2 T}{\partial r^2} \quad \text{Equation 1B}$$

Sperical coordinates:

$$\rho C_p \frac{\partial T}{\partial \theta} = \rho(-\Delta H_R)a e^{-\Delta E/RT} + k \frac{1}{r^2} \frac{\partial}{\partial r}\left(r^2 \frac{\partial T}{\partial r}\right) \quad \text{Equation 1C}$$

Where:
$\rho$ = density
$C_p$ = heat capacity
$T$ = temperature
$\theta$ = time
$\Delta H_R$ = heat of reaction
$a$ = Arrhenius pre-exponential factor
$\Delta E$ = activation energy
$R$ = gas constant
$k$ = thermal conductivity
$r$ = location in the solid Under the steady-state conditions of the calorimeter, the left side of Equation 1A is zero. Therefore, the differential equation describing the critical condition in cylindrical coordinates is the following:

$$\rho(-\Delta H_R)a e^{-\Delta E/RT} = -k \frac{1}{r} \frac{\partial}{\partial r}\left(r \frac{\partial T}{\partial r}\right) \quad \text{Equation 2}$$

The density of the solid ($\rho$) is easily measured in the lab, and the heat capacity ($C_p$) is measured or estimated from the literature. The thermal conductivity (k) of the solid is determined by Fourier's law from calorimeter experimental data well below the reaction conditions (if not known from the literature). The only remaining unknowns in the equation are thus the activation energy ($\Delta E$), the heat of reaction ($\Delta H_R$), and the pre-exponential factor (a).

The heat of reaction and pre-exponential factor may be lumped together into a single constant $(-\Delta H_R)a$. Since there are thus only two unknowns in Equation 2, solution is possible utilizing the two sets of boundary conditions, i.e., critical hot surface and corresponding cold surface temperatures as generated by the experimental data. This is accomplished through a numerical solution of Equation 2 on a computer as shown below.

Derivation and Solution of Equation 2

The derivation and numeric solution of Equation 2 is presented below using the following symbols:

r = specific location in the solid sample
$r_c$ = cold surface radius
$r_h$ = hot surface radius
h = axial length of the sample reaction chamber
$\Delta r$ = an incremental radial distance in the sample
$T_r$ = local temperature of the solid at location r
$T_c$ = cold surface temperature
$T_h$ = the critical hot surface temperature Writing on energy balance around an incremental cylinder in the calorimeter system:

| Heat conducted out | − | Heat conducted in | = | Heat generated by reaction. |
|---|---|---|---|---|

Expressing each term of the energy balance equation mathematically:

$$\text{Heat conducted out} = \frac{kh2\pi \left(r + \frac{\Delta r}{2}\right)\left(T_{r+\Delta r} - T_r\right)}{\Delta r}$$

$$\text{Heat conducted in} = \frac{kh2\pi \left(r + \frac{3\Delta r}{2}\right)\left(T_{r+2\Delta r} - T_{r+\Delta r}\right)}{\Delta r}$$

$$\text{Heat generated by reaction} = 2h\pi \Delta r \left(r + \frac{\Delta r}{2}\right) \rho(-\Delta H_r) a e^{-\Delta E/RT_{avg}}$$

where: $T_{avg} = \frac{T_r + T_{r+\Delta r}}{2}$

Therefore, substituting the terms of the energy balance gives:

$$\frac{kh2\pi \left(r + \frac{\Delta r}{2}\right)\left(T_{r+\Delta r} - T_r\right)}{\Delta r} -$$

$$\frac{kh2\pi \left(r + \frac{3\Delta r}{2}\right)\left(T_{r+2\Delta r} - T_{r+\Delta r}\right)}{\Delta r} =$$

$$2h\pi \Delta r \left(r + \frac{\Delta r}{2}\right) \rho(-\Delta H_R) a e^{-\Delta E/RT_{avg}}$$

Dividing by $2h\pi \Delta r(r+(\Delta r/2))$ gives:

$$-\frac{k}{\left(r + \frac{\Delta r}{2}\right)\Delta r}\left[\left(r + \frac{3\Delta r}{2}\right)\left(\frac{T_{r+2\Delta r} - T_{r+\Delta r}}{\Delta r}\right) - \left(r + \frac{\Delta r}{2}\right)\left(\frac{T_{r+\Delta r} - T_r}{\Delta r}\right)\right]$$

$$= \rho(-\Delta H_R) a e^{-\Delta E/RT_{avg}} \qquad \text{Equation 3}$$

Taking the limit of Equation 3 as $\Delta r \to 0$ gives:

$$-k\frac{1}{r}\frac{d}{dr}\left(r\frac{dT}{dr}\right) = \rho(-\Delta H_r) a e^{-\Delta E/RT} \qquad \text{Equation 2}$$

This is the differential equation describing the critical condition point of the calorimeter system. This equation does not possess an exact integral and, therefore, must be solved numerically on a computer using Equation 3, the finite form of differential Equation 2.

Solution of Equation 3 is simplified by noting that the thermal gradient of the reacting sample at the hot surface is zero, thus re-expressing Equation 3 below at the location $r = r_h - \Delta r$, as:

$$k\left(\frac{T_{rh} - T_{rh-\Delta r}}{\Delta r}\right) = \rho(-\Delta H_R) a e^{-\Delta E/RT_{avg}} \qquad \text{Equation 4}$$

The boundary conditions which are used for solution of Equations 3 and 4 to determine the unknown kinetic values, i.e., $\Delta E$ and $(-\Delta H_R)a$, are the critical temperatures from the experimental data below:

Critical Point #1: $T_{rh} = T_{h1}$, $T_{rc} = T_{c1}$

Critical Point #2: $T_{rh} = T_{h2}$, $T_{rc} = T_{c2}$

A typical numerical computer solution for the equation is given below. The solution of Equations 3 and 4 is determined iteratively, that is, $\Delta E$ and $(-\Delta H_R)a$ are varied until the equation is satisfied for both sets of boundary conditions.

1. Assume a $\Delta E$.
2. Assume a $(-\Delta H_R)a$.
3. Substitute $T_{h1}$, $\Delta E$, and $(-\Delta H_R)a$ into Equations 3 and 4.
4. Using Equation 4, start $T_{rh-\Delta r}$ at $T_{h1}$ and decrease $T_{rh-\Delta r}$ incrementally until two sides of the equation are most equal.
5. Substitute $T_{r+2\Delta r} = T_{h1}$, $T_{r+\Delta r} = T_{rh-\Delta r}$, and $r = r_h - \Delta r$ into Equation 3. Start $T_{rh-2\Delta r}$ at $T_{rh-\Delta r}$ and decrease $T_{rh-2\Delta r}$ incrementally until the two sides of the equation are most equal.
6. Repeat step 5 while incrementing r down by $\Delta r$. Do until $r = r_c$, therefore, finding the temperature distribution inside the calorimeter.

7. Compare $T_{rc}$ with $T_{c1}$. Vary $(-\Delta H_R)a$ by a fixed increment and repeat steps 3-6 until $T_{rc}$ and $T_{c1}$ are most equal. At this point, values of $\Delta E$ and $(-\Delta H_R)a$ have been found so that Equation 4 is satisfied for critical point No. 1.
8. Repeat steps 2-7 to determine $(-\Delta H_R)a$ for critical point No. 2 for the same $\Delta E$.
9. Compare the two $(-\Delta H_R)a$ values. Increase $\Delta E$ incrementally and repeat steps 2-8 until the $(-\Delta H_R)a$ values are most equal.

Therefore, values of $\Delta E$ and $(-\Delta H_R)a$ have been found which satisfy the system for the two boundary conditions. These, then, are the kinetic parameters describing the decomposition reaction.

Application of the Kinetics Results

The known kinetics now allow determination of the adiabatic unsteady-state thermal decomposition of the solid. Since adiabatic conditions imply that the third term, the heat transfer term, of Equation 1 is zero, the equation describing this condition is the following (independent of the coordinate system):

$$C_p \frac{dT}{d\theta} = (-\Delta H_R)a e^{-\Delta E/RT} \qquad \text{Equation 5}$$

Integration of this equation numerically on a computer yields the adiabatic time to explosion curve for the solid starting at any temperature. Thus assuming a given initial temperature, the equation solves for the length of time for the product to reach explosion.

Since the heat transfer characteristics of the solid are known, prediction of the nonadiabatic thermal decomposition of the solid is also possible. Numerical integration of Equation 1 on a computer yields the unsteady-state behavior of the solid for any starting temperature, geometry, and known heat loss characteristics to the environment. Two results are possible for a reactive solid under nonadiabatic conditions. If the solid is at a relatively low temperature, it will be exothermically decomposing at a very slow rate. Any heat generated by reaction is conducted away from the solid to the surroundings, thus preventing the solid from undergoing a thermal runaway. The time to explosion at this starting temperature is, therefore, infinite; that is, the solid will cool off. At higher temperatures, however, the solid will be decomposing at a much greater rate and, therefore, generating much more heat. If this generation is greater than the heat loss capabilities, the solid will thermally run away. The time to explosion under these nonadiabatic conditions will be slightly longer than if it were adiabatic.

Nearly adiabatic conditions can occur in well-insulated process equipment such as dryers. The adiabatic time to explosion information is used to establish safe operating conditions for the equipment. Nonadiabatic conditions can occur in storage of solid materials. Fiber paks and tote bins are examples where heat transfer to the environment is appreciable. The nonadiabatic time to explosion information is used to determine if the material is stable enough for long term storage at prescribed conditions.

Example

The following is an account of two solids calorimeter runs on dry Dowicil ® 200 antimicrobial sample (Registered Trademark of The Dow Chemical Company).

Approximately 35 grams of sample is loaded into the calorimeter. The cooling water (about 20° C.) for the inner pipe is turned on and allowed to steady out. A slow ramp of about 2° C. per minute is started on the outer heater and continued until the system then becomes unstable and undergoes a thermal runaway. The critical hot surface temperature is determined to be 178° C. and the corresponding cold surface temperature is measured at 25° C.

The calorimeter is again loaded with sample. Conditions for this experiment are changed by flowing hot water (about 90° C.) through the inside pipe. In this experiment, the critical hot surface temperature is determined to be 156° C. and the corresponding cold surface temperature is measured at 94° C.

Using these two data points, or boundary conditions, in a computer program to solve Equation 2, a $\Delta E$ of 29,000 cal/mole and $(-\Delta H_R)a$ of $1.41 \times 10^{14}$ cal/g-sec. is calculated as shown in Table I. From these parameters, the time to explosion curve is generated from the solid under adiabatic conditions (Table II) and nonadiabatic conditions (Table III). This hazard information is used to determine safe operating and storage conditions for this chemical.

Table I

CALORIMETER CALCULATIONS FOR DOWICIL ® 200 ANTIMICROBIAL

Calorimeter Experimental Data:
Density = 40.0 lb/ft³
Heat capacity = 0.35 cal/g-°C.
Thermal conductivity = 0.0026 w/cm-°C.
Heater Diameter = 1.05 in
Cooler Diameter = 0.40 in
Critical Temp. #1 = 178° C.
Coolant Temp. #1 = 25° C.
Critical Temp. #2 = 156° C.
Coolant Temp. #2 = 94° C.

Calculated Results:
$\Delta E$ = 29,000 cal/mole
$(-\Delta H_R)a = 1.41 \times 10^{14}$ cal/g-sec.

Table II

ADIABATIC RUNAWAY PREDICTION FOR DOWICIL ® 200 ANTIMICROBIAL

Heat Capacity = 0.35 cal/g-°C.
Calculated $\Delta E$ = 29,000 cal/mole
Calculated $(-\Delta H_R)a = 1.41 \times 10^{14}$ cal/g-sec.

Time to explosion for dry Dowicil ® 200 under adiabatic conditions

| Starting Temp. of Solid (°C.) | Time to Explosion |
|---|---|
| 20 | 2.042 Yrs |
| 30 | 154.445 Days |
| 40 | 35.459 Days |
| 50 | 8.936 Days |
| 60 | 58.824 Hrs. |
| 70 | 17.430 Hrs. |
| 80 | 5.543 Hrs. |
| 90 | 1.881 Hrs. |
| 100 | 40.628 Min. |
| 110 | 15.453 Min. |
| 120 | 6.183 Min. |
| 130 | 2.592 Min. |
| 140 | 1.135 Min. |
| 150 | 31.043 Sec. |
| 160 | 14.691 Sec. |
| 170 | 7.199 Sec. |
| 180 | 3.644 Sec. |
| 190 | 1.902 Sec. |
| 200 | 1.021 Sec. |

TABLE III

NON-ADIABATIC RUNAWAY PREDICTION FOR DOWICIL® 200 ANTIMICROBIAL

Density = 25.0 lb/ft$^3$

Heat Capacity = 0.35 cal/g-°C.

Thermal Conductivity = 0.0026 w/cm-°C.

Calculated $\Delta E$ = 29,000 cal/mole

Calculated $(-\Delta H_R)a = 1.41 \times 10^{14}$ cal/g-sec.

Cylindrical geometry

Diameter of solid = 38.00 cm

Ambient air temperature = 25.0° C.

Film heat transfer coefficient = 1.00 Btu/hr-ft$^2$-°F.

Time to explosion curve for dry Dowicil 200® under nonadiabatic conditions

| Starting Temp. of Solid (°C.) | Time to Explosion |
|---|---|
| 30 | Cooled |
| 40 | Cooled |
| 50 | Cooled |
| 60 | Cooled |
| 70 | Cooled |
| 80 | Cooled |
| 90 | Cooled |
| 100 | 40.628 Min. |
| 110 | 15.453 Min. |
| 120 | 6.183 Min. |
| 130 | 2.592 Min. |
| 140 | 1.135 Min. |
| 150 | 31.043 Sec. |
| 160 | 14.691 Sec. |
| 170 | 7.199 Sec. |
| 180 | 3.644 Sec. |
| 190 | 1.902 Sec. |
| 200 | 1.021 Sec. |

What is claimed is:

1. The method of quantifying the kinetic constants $\Delta E$, the activation energy, and $(-\Delta H_R)a$, the product of heat of reaction and Arrhenius pre-exponential factor, for a given thermally unstable solid, comprising the steps of:
   (1) locating a sample between controlled hot and cold surfaces, and applying a first known thermal gradient to the sample;
   (2) gradually raising the temperature of the hot surface to determine the maximum temperature that the sample can withstand without undergoing a thermal runaway, and defining that temperature as the critical temperature for that applied gradient;
   (3) repeating steps (1) and (2) at a second and different known applied thermal gradient, to obtain a second and different critical temperature; and
   (4) solving the steady-state differential equation describing the calorimeter system for $\Delta E$ and $(-\Delta H_R)a$ using the critical temperatures and corresponding cold surface temperatures as boundary conditions.

* * * * *